United States Patent [19]

Hall, Jr. et al.

[11] 4,229,612
[45] Oct. 21, 1980

[54] DECOLORIZATION OF NORBORNADIENE DIMERS

[75] Inventors: Lewis W. Hall, Jr., Chadds Ford, Pa.; David L. Kerr; Elmer J. Hollstein, both of Wilmington, Del.; Harry K. Myers, Jr., Aston Township, Chester County; Abraham Schneider, Overbrook Hills, both of Pa.

[73] Assignee: Suntech, Inc., Philadelphia, Pa.

[21] Appl. No.: 7,112

[22] Filed: Jan. 29, 1979

[51] Int. Cl.$^2$ .............................................. C07C 13/28
[52] U.S. Cl. .................................. 585/823; 208/307; 585/824; 585/360; 149/109.4; 60/208
[58] Field of Search ................. 585/823, 824; 208/307

[56] References Cited

U.S. PATENT DOCUMENTS

| | | | |
|---|---|---|---|
| 1,636,938 | 7/1927 | Kauffman | 208/307 |
| 1,836,577 | 12/1931 | Cross | 208/307 |
| 1,838,621 | 12/1931 | Haseman | 208/307 |
| 1,866,590 | 7/1932 | Baylis | 208/307 |
| 1,992,979 | 3/1935 | Wollner | 208/307 |
| 3,394,200 | 7/1968 | Sargent | 585/824 |

OTHER PUBLICATIONS

T. J. Katz et al., Tetrahedron Letters, No. 27, 2601–2605, 1967.
Nancy Acton et al., J. Amer. Chem. Soc., 94, 15, 1972.
Thomas J. Katz et al., J. Amer. Chem. Soc., 91, 206, 1969.
Chem. Ab. 70:87128q, 1969; 2410c, 1948; 55:23951a, 1961, 44:4507i, 1950; 86:22242h, 1977; 81:103421q, 1974.
Chem. Ab. 79:68067p, 1973; 73:5221q, 1970; 68:52872j, 1968; 71:64473e, 1969; 70:69460n, 1969.

*Primary Examiner*—Veronica O'Keefe
*Attorney, Agent, or Firm*—J. Edward Hess; Donald R. Johnson; Anthony Potts, Jr.

[57] ABSTRACT

The removal of color bodies from an olefinic or saturated endo-endo hexacyclic homodimer of norbornadiene or mixtures thereof is accomplished by the use of a serpentine clay. Also acid bentonite clay or a montmorillonite clay can be used to remove the color bodies from the saturated dimer. The saturated dimer has a high density and a high heat of combustion making it useful as a missile fuel. Removal of the color bodies avoids possible catalyst poisoning in the hydrogenation of the olefinic to the saturated dimer. Also removal of the color bodies from the saturated dimer eliminates the possible problem of a material precipitating out on engine turbine blades and causing maintenance or operational problems.

13 Claims, No Drawings

DECOLORIZATION OF NORBORNADIENE DIMERS

BACKGROUND OF THE INVENTION

The invention herein described was made in the course of or under a contract thereunder with the United States Air Force Systems Command.

This invention relates to the purification of an olefinic endo-endo hexacyclic homodimer of norbornadiene or a mixture of isomers of said dimers of norbornadiene. The dimer or mixture of the dimers and its isomers hereinafter will be referred to as OHDNB. The invention also relates to the purification of the saturated endo-endo hexacyclic homodimer of norbornadiene or a mixture of the dimers and its isomers. The saturated dimer or a mixture of the dimers and its isomers hereinafter will be referred to as SHDNB.

Particularly the invention relates to removal of "color bodies" from OHDNB or SHDNB. "Color bodies" are color imparting substances which impart color to the liquid OHDNB or SHDNB. Often the color is a yellow ranging from a tint to a deep yellow. Some of the color bodies could be small amounts of organometallic catalyst used to form the dimer from the monomer. OHDNB and SHDNB without color bodies have the appearance of pure water.

Norbornadiene (bicyclo-(2.2.1)-2,5-heptadiene) can be prepared by reacting cyclopentadiene and acetylene at an elevated temperature, see U.S. Pat. No. 2,875,256 (Cl 260–666). Norbornadiene has the following structure:

It can be dimerized into olefinic hexacyclic homodimers, one of which has the following structure:

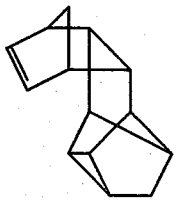

I

Dimerization of norbornadiene to compound I is disclosed in "The Stereochemical Course of Metal Catalyzed Cycloaddition Reactions of Norbornadiene", T. J. Katz et al, Tetrahedron Letters, No. 27, pp 2601–2605, 1967. The dimerization involves the use of a group VIII metal complex.

Among the compounds that can be formed from contacting compound I with hydrogen iodide is a compound having the following structure II.

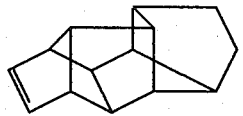

II

This is disclosed in "Dimerization and Trimerization of Norbornadiene by Soluble Rhodium Catalysts", Nancy Acton et al., Journal of the American Chemical Society, 94:15, July 26, 1972. Compound II, along with compound I is also disclosed in Chemical Abstracts, Vol. 70, 1969, page 265, 87128q disclosed in Journal of the American Society, 91:1, June 1, 1969, pages 206–8.

Hydrogenation of compounds I or II or an isomeric mixture containing them results in a compound or a mixture having a high density and a high heat of combustion making it useful as a missile fuel in either jet or rocket propulsion. The structure of the hydrogenated compound is as follows:

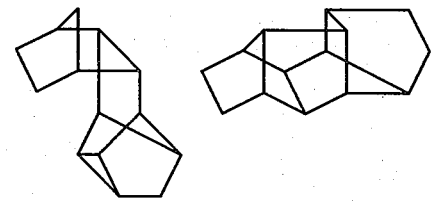

Jet propulsion includes a jet engine which can be used for a missile, an aircraft and others and includes the three basic types, i.e., ramjet, turbojet and pulse jet. The term rocket generally refers to a device containing its own oxygen or oxidizing agent. An article in Aviation Week and Space Technology, Jan. 26, 1976, pages 111–113 discloses some of the high density hydrocarbon fuels that are under consideration as missile fuels.

However, the color bodies in OHDNB can diminish the activity of a hydrogenation catalyst used to convert the OHDNB to SHDNB. Furthermore the color bodies in the SHDNB can precipitate upon engine turbine blades and cause operational and maintenance problems. Thus it is advantageous to remove the color bodies from the aforementioned materials. Surprisingly, as discussed hereinafter, it has proven difficult to remove the color bodies.

The use of various clays as a decoloring agent in the treatment of hydrocarbons is known, see Encyclopedia of Chemical Technology, Kirk-Othmer, 2nd Edition, Vol 5, Clay (Survey). The foregoing reference classifies clays as to their geographic origin, chemical composition, and use. Serpentine mineral clays are classified as analogous to kaolin in which the latter's aluminum is replaced by magnesium. Thus a serpentine mineral clay can be considered as consisting of $Mg_3Si_2O_5(OH)_4$, or a variation thereof, but as with all clays other minerals can be present. Synthetic clays such as one consisting of magnesium silicon, oxygen and hydrogen can also be prepared. Use of a magnesium silicate as a decolorization agent is disclosed in the following Chemical Abstracts, 1948, 2410 c; Vol 55, 23951 a; Vol 44, 4607 i; and Vol 86, 1977, page 372, 86; 22242 h. A bentonite clay is one rich in montmorillonite which contains both magnesium and aluminum and certain cations such as sodium as well as other elements. Generally, while bentonite differs from a montomorillonite clay in its geologic origin, either type can be used for decolorizing. Use of a bentonite or a montmorillonite for decoloring is disclosed in the following Chemical Abstracts: Vol 81, 1974, page 365, 103421q; Vol 79, 1973, page 97, 68067 p; Vol 73, 1970, page 86, 5221 q; Vol 68, 1968, page 5137, 52872 j; Vol 71, 1969, page 254, 64473 e; and Vol 70, 1969, page 72, 69460 n. A bentonite clay which has been washed with acid such as hydrochloric, sulfuric, phosphoric and the like is referred to as an acidic bentonite clay.

SUMMARY OF THE INVENTION

Color bodies, formed during the conversion of the norbornadiene to hexacyclic dimers, maintain a tenacious relationship with the dimer. These color bodies can be removed readily from OHDNB by contacting the dimer with a serpentine mineral clay whereas their removal from SHDNB can be achieved by contacting with a serpentine mineral clay, a montmorillonite mineral clay or an attapulgite clay. With SHDNB mixtures of the aforementioned clays can be used.

One of the useful clays is a serpentine mineral clay, of which magnesium silicate is one example. The latter is commercially available as "Florisil" which is a trademark for a highly selective adsorbent of extremely white granular or powdered magnesia-silica gel. The clay can be heated slightly to drive off adsorbed water prior to its use. A synthetic clay can also be used.

Another useful clay is acidic bentonite clay. Bentonite refers to a colloidal clay containing montmorillonite. A montmorillonite clay itself can be used. The acidic means that the clay has been treated with acid or formed within an acid environment. One acidic bentonite clay is commercially available as "Superfiltrol" which name is a trademark. Still another useful clay is attapulgite. Mixtures of the aforementioned clays can also be used. The clays can be synthetic as well as natural.

The amount of the clay used to contact the dimers can vary substantially. The amount of clay used should be sufficient to remove the color bodies, while an excessive amount should be avoided because of unnecessary expense. The optimum amount depends upon many variables such as the amount of color bodies present, the duration of contact and the type of contacting and the amount of norbornadiene dimer contacted. Generally the weight ratio of the clay to the dimer used for contacting is in the range between from about 0.05 to about 1.

The time required for contacting the dimer with the clay can also vary substantially. The contacting should continue until the dimer is decolorized to the desired level. Often the decolorization is substantial. The desired level is that which is necessary to avoid catalyst poisoning and/or deposits on engine turbine blades. Many variables influence the time requirement. Among them are the relative amounts of color bodies present and the amount of removal desired.

The amount of decolorization that occurs as a result of a treatment can be measured by various known colorimetry methods including the Saybolt method. For the OHDNB a minimum acceptable Saybolt color would be about +20 ±2. At that value the liquid could be described as having an off-color or tinted appearance. For the SHDNB a higher Saybolt color is preferred, i.e. about a +25 with a +30 more preferred. At about a +30 Saybolt color the liquid can be described as having a water-like clear appearance. After the desired decolorization has occurred the treated liquid is separated from the clay by known means, such as filtration.

The following examples are illustrative of the present invention. Also shown are comparative examples. Also described is a method for preparing the isomers and mixtures thereof.

EXAMPLES

The isomerization of an olefinic endo-endo dimer having structure I was achieved in the following manner. Acidic alumina catalyst, 131.6 grams, and 3270 grams of yellow dimer were mixed together in a suitable flask at 25° C. and then deaerated under argon for about twenty minutes with stirring. After the deaeration the mixture was heated gradually over about two hours to a temperature of about 170° C. During this period some moisture was driven off. Intermittent heating occurred over about 37.6 hours and during that time the temperature reached a maximum of about 207° C. During the isomerization the alumina developed an orange color while the liquid became a light yellow. The conversion via vapor phase chromatography was about 75 wt. % and the selectivity as to Compound II was about 74%.

An attempt was made to remove the yellow color of the foregoing liquid isomeric mixture products (OHDMB), which could cause poisoning of a hydrogenation catalyst or foul engine blades. A sample of the OHDNB was contacted with 7.5 wt. % of "Superfiltrol" clay (acidic bentonite) which had been dried (activated) for two hours at 100° C. However, a violent exotherm occurred as the dry clay was slowly added to the stirred dimer. As a result dark color bodies formed on the clay without any removal of the yellow coloration of the isomeric mixture.

Another attempt to remove the yellow color of the OHDNB involved stirring overnight a sample of the liquid with a 90/10 mixture of unactivated attapulgite and "Superfiltrol" clays. No exotherm was evident and no apparent reduction of the yellow color was found on filtering the clay from the liquid.

Another OHDNB sample was then percolated through 14.8 wt. % of basic alumina (aluminum oxide, $Al_2O_3$) which had been dried one hour at 100° C. Again, no decrease in color was apparent. Still another sample was percolated through 38.6 wt. % of silica gel (dried one hour at 147° C.) with no improvement evident.

Finally, another OHDNB sample was percolated through 21.8 wt. % of 100-200 mesh magnesium silicate (one available commercial product is "Florisil") in a 4.4 cm. diameter column. The silicate had previously been dried by heating for ½ hour at 145° C. The olefin filtrate showed a marked reduction in color. Results of analyses performed on this sample of purified olefinic dimer are as follows: Fe, <0.1 ppm, Al <0.1 ppm (via atomic absorption), Cl 38.1 ppm (via Dohroman colometry), phosphorous 0.3 ppm (via wet test method), and Saybolt color +19.

Some of the foregoing isomeric mixture (OHDNB) was completely and rapidly hydrogenated in a rocking bomb using 10 wt. % of powdered 5% rhodium-on-alumina catalyst at a maximum temperature of 125° C. and 100 psig of hydrogen by shaking for about 77 minutes. After filtration to remove the hydrogenation catalyst the final hydrogenated product (SHDNB) was a clear, very pale yellow with a pour point of about −25° C.

A sample of the SHDNB was decolorized in the following manner. 3000 grams of SHDNB were contacted while stirring with 300 grams of a mixture consisting of about 10% acid bentonite and about 90% attapulgite in a four liter erlenmeyer flask for about 19 hours. The resulting mixture was filtered and a +30 Saybolt color filtrate was obtained. Two hours of contact under the same conditions did not result in a satisfactory decolorization.

We claim:

1. Process for the decolorization of an olefinic hexacyclic dimer of norbornadiene comprising contacting a dimer selected from a group consisting of isomers having the following structures or a mixture thereof:

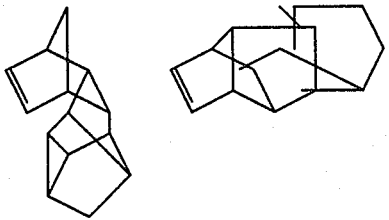

with a natural or synthetic serpentine clay and continuing the contacting until decolorization occurs.

2. Process according to claim 1 wherein the serpentine clay is free from adsorbed water.

3. Process according to claim 2 wherein the weight ratio of the serpentine clay to the dimer is in the range between from about 0.05 to about 1.

4. Process according to claim 2 wherein the contacting continues until the dimer is substantially decolorized.

5. Process according to claim 1 wherein the serpentine clay is a magnesium silicate.

6. Process according to claim 5 wherein the weight ratio of the clay to the dimer is in the range between from about 0.05 to about 1 and the contacting continues until the dimer has at least a Saybolt color of about +20 ±2.

7. Process according to claim 6 wherein after the decolorization occurs the dimer is separated from the clay.

8. Process for the decolorization of a saturated hexacyclic dimer of norbornadiene comprising contacting a dimer selected from a group consisting of dimers having the following structures or a mixture thereof:

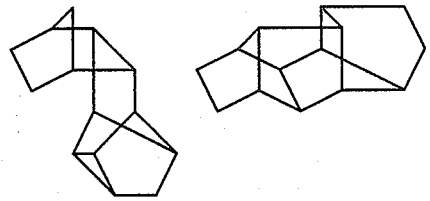

with a natural or synthetic clay selected from the group consisting of serpentine clay, montmorillonite clay, acidic bentonite, attapulgite and mixtures of the aforementioned clays and continuing the contacting until decolorization occurs.

9. Process according to claim 8 wherein the weight ratio of the clay or a mixture of the clays to the dimer is in the range between from about 0.05 to about 1.

10. Process according to claim 9 wherein the contacting continues until the dimer is substantially decolorized.

11. Process according to claim 10 wherein the clay is a mixture of acidic bentonite and attapulgite.

12. Process according to claim 11 wherein the weight ratio is in the range between from about 0.05 to about 1 and the contacting continues until the dimer has a Saybolt color of at least about +25.

13. Process according to claim 12 wherein after the decolorization occurs the dimer is separated from the clay.

* * * * *